(12) United States Patent
Emmenegger et al.

(10) Patent No.: US 6,605,041 B2
(45) Date of Patent: Aug. 12, 2003

(54) 3-D ULTRASOUND RECORDING DEVICE

(75) Inventors: Niklaus Emmenegger, Zurich (CH); Olaf Engfer, Zurich (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/968,822

(22) Filed: Oct. 2, 2001

(65) Prior Publication Data

US 2002/0062077 A1 May 23, 2002

Related U.S. Application Data

(63) Continuation of application No. 09/242,565, filed as application No. PCT/CH97/00311 on Aug. 22, 1997, now Pat. No. 6,296,613.

(30) Foreign Application Priority Data

Aug. 22, 1996 (CH) ............................................. 2062/96

(51) Int. Cl.[7] ................................................. A61B 8/00
(52) U.S. Cl. ...................................................... 600/443
(58) Field of Search ................................. 600/437, 445, 600/407, 414, 426, 443, 447, 427; 128/916

(56) References Cited

U.S. PATENT DOCUMENTS

| | | | | | |
|---|---|---|---|---|---|
| 5,800,352 A | * | 9/1998 | Ferre et al. | ................. | 128/897 |
| 5,891,034 A | * | 4/1999 | Bucholz | ..................... | 600/426 |
| 5,911,691 A | * | 6/1999 | Mochizuki et al. | ......... | 600/443 |
| 6,122,538 A | * | 9/2000 | Sliwa et al. | ........... | 324/207.14 |
| 6,186,948 B1 | * | 2/2001 | Kamiyama et al. | ......... | 600/443 |
| 6,186,949 B1 | * | 2/2001 | Hatfiled et al. | ............. | 600/443 |

* cited by examiner

*Primary Examiner*—Marvin M. Lateef
*Assistant Examiner*—Maulin Patel
(74) *Attorney, Agent, or Firm*—Pennie & Edmonds LLP

(57) ABSTRACT

The present invention is related to a device for recording three-dimensional ultrasound images. The device includes an ultrasound head which can be freely moved by hand, an ultrasound recording apparatus, an image processing system, and a position detection system. The position detection system has an analyzing unit and at least two sensors for detecting electromagnetic waves so that the position and orientation of the ultrasound head and, thus, the position and orientation of the ultrasound section images in space can be determined.

19 Claims, 4 Drawing Sheets

3-D ULTRASOUND RECORDING DEVICE

RELATED APPLICATIONS

The present application is a continuation of U.S. application Ser. No. 09/242,565 filed Feb. 19, 1999, now U.S. Pat. No. 6,296,613 which is a 371 of PCT/CH97/00311, filed Aug. 22, 1997, which application is incorporated herein in its entirety.

FIELD OF THE INVENTION

The present invention relates to an ultrasound imaging system having an ultrasound head for and processor for obtaining three-dimensional ultrasound images.

BACKGROUND OF THE INVENTION

A system for determining the position of a sensor within a given object and for the display of previously recorded images of the object corresponding to the sensor position has been described earlier by BUCHHOLZ in U.S. Pat. No. 5,383,454. With that system it is also possible to guide the tip of a sensor to a particular location within an object, while the position of the sensor can be observed on a monitor screen which also displays a previously recorded image of that particular region within the object. In that earlier concept, the position of the sensor is determined using a commercially available, three-dimensional sound digitizer.

Another example of a system for the acquisition of three-dimensional ultrasound image data is described by POLZ in the European patent EP 0 736 284 A2. That system incorporates an ultrasound scanning head. A sensor, which includes receiver coils to pick up magnetic fields emitted by a transmitter, produces sensor output data (both positional and rotational data) which precisely define the spatial position and orientation of the ultrasound scanning head. These are translational X, Y and Z axis data as well as rotational data around these axes.

A prerequisite for sufficiently precise positional and orientational determinations using magnetic field measurements is very detailed information on such extraneous parameters as:

interference fields generated for instance by display monitors, computers or electric motors;

interference patterns produced by highly permeable materials in the magnetic field, for instance metal objects moving within the measuring region; or electromagnetic interference fields emanating from AC power supplies.

Quantifying these effects and/or minimizing them by appropriate hardware or procedures, be it shielding or continuous calibration, is a complex matter. The drawback of the earlier concept referred to thus lies in the fact that it is difficult to obtain positional and orientational determinations with the necessary degree of accuracy.

Another system for the acquisition of ultrasound images with the aid of a freely movable, manually guided ultrasound scanning head has been described by NOWACKI in U.S. Pat. No. 5,197,476. This earlier design is used for locating a target object within the human body. The system encompasses a table-mounted three-dimensional frame equipped with a number of infrared light-emitting diodes, a pair of infrared cameras for capturing the radiation emitted by the infrared LEDs, a computer and an ultrasound probe which itself is provided with infrared LEDs. Prior to applying the infrared probe the frame is mounted on the table and by means of the cameras the position of the infrared LEDs is measured and stored in the computer. The human body is then positioned within or directly next to the reference volume.

The freely manipulable, manually guided ultrasound probe is moved within the reference volume defined by the three-dimensional frame in a manner that the ultrasound probe remains within the measuring range of the cameras. The computer compares the position of the infrared light emitting diodes mounted on the ultrasound probe with the starting positions of the infrared LEDs on the three-dimensional frame, which permits both the very precise determination of the position of the ultrasound probe and the display of the position of the target object on a computer monitor screen. The drawback of this earlier invention lies in the fact that the ultrasound images can be acquired only within the reference volume predefined by means of the three-dimensional frame.

A method for the determination of the position and orientation of a platform in space has been disclosed by DI MATTEO in U.S. Pat. No. 4,396,945. The devices serving to unambiguously identify the three light sources mounted on the platform include three light modulators positioned between the light source and the fiber optic links. A code generator supplies each of the three light modulators with a unique code which produces an on-off modulation of each individual light source. In a modified version of this earlier method, unambiguous identification of each light source is obtained by providing each light source with a color reflector which reflects a specific color that differs from that of the other light sources. The drawback of this earlier invention lies in the fact that it is necessary to equip the three light sources, mounted on the moving object, with on-off modulation or, in the case of reflectors, with color coding provisions.

SUMMARY OF THE INVENTION

One embodiment of the present invention is related to a system for providing a means for acquiring three-dimensional ultrasonographic images using a freely movable, manually guided ultrasound scanning head, an ultrasound acquisition device and a positional-determination i.e. locating device, which locating device permits the determination of the position and orientation of the ultrasound scanning head and thus of the spatial position and orientation of the tomographic ultrasound images relative to a given base, preferably by linear measurements.

Another embodiment of the present invention relates to an ultrasound imaging system for creating a three-dimensional ultrasound image of a patient body. An ultrasound scanning head is configured to acquire a plurality of ultrasound images having a known orientation with respect to the ultrasound scanning head. An optical position determining device determines a position and orientation of the ultrasound scanning head. By optical it is meant that the position determining device uses electromagnetic waves, preferably light, to determine the position and orientation of objects, such as the ultrasound scanning head. An image processor relates the plurality of ultrasound images to one another to create the three-dimensional ultrasound image of the body.

In a preferred embodiment, the optical position determining device is further configured to determine a position and orientation of the patient body. In a more preferred embodiment, the system, such as via the image processor, is configured to determine the position and orientation of the ultrasound images with respect to the patient body. The system can be configured to determine the position and orientation of the three-dimensional ultrasound image with respect to the body.

The present invention makes it possible for the base that serves to identify the position of the ultrasound probe to be constituted of receivers, meaning, for example, the very cameras that serve to record the position of the ultrasound probe.

The system of the present invention is not affected by external parameters, is easy to handle; even if the positional determination were to be disrupted for instance by an object that strayed in between the acquisition device and the ultrasound scanning head, measurements can continue as soon as a clear view is restored, and the tracking accuracy is not negatively affected by extraneous electromagnetic fields produced by display monitors and/or electrical equipment.

Another embodiment of the present invention relates to an ultrasound imaging system for creating a three-dimensional image of a patient body. The system includes an ultrasound scanning head for acquiring a plurality of ultrasound images, a fixed control plane for determining position and orientation of the ultrasound scanning head relative to a spatial base by linear measurement, transmitters for emitting electromagnetic waves associated with either base points on the spatial base or control points on the control plane, receivers for receiving the electromagnetic waves located on the other of the base points or the control points, and an image processor for processing the ultrasound images to create the three-dimensional image of the body. The electromagnetic waves are used to determine the position and orientation of the ultrasound scanning head to thereby position and orient the plurality of ultrasound images.

In another aspect of the present invention, the ultrasound imaging system includes a freely movable, manually guided ultrasound scanning head for acquiring a plurality of ultrasound images, an ultrasound acquisition device for storing and displaying the plurality of ultrasound images, an image processor for processing the plurality of ultrasound images to create the three-dimensional image of the body, and a positional locating device for determining position and orientation of the ultrasound scanning head to thereby position and orient the plurality of ultrasound images. The locating device has a plurality of electromagnetic wave emitting devices located on the ultrasound scanning head, a plurality of electromagnetic wave sensor arrays for detecting the electromagnetic waves of the emitting devices, and an evaluation unit for computing the position and orientation of the ultrasound scanning head relative to a spatial base by linear measurements based on the electromagnetic waves.

The means provided on the ultrasound scanning head to emit electromagnetic waves for positional and orientational determinations are in the form of optical light sources infrared light emitting diodes (IRLEDs), reflectors, electrofluorescent reflectors, or fiber optics connected to a light source.

In yet another embodiment of the invention, the sensor systems serving to detect the electromagnetic waves within the measuring region are in the form of spatially fixed, unidimensional (linear-array) cameras, allowing an evaluation unit to determine the position and orientation of the ultrasound scanning head and thus the spatial position and orientation of the tomographic ultrasound images. The sensor systems serving to detect the electromagnetic waves within the measuring region are preferably cameras which are not spatially fixed, the position of the cameras being detectable by the acquisition and evaluation of a spatially fixed control-point reference field which in turn allows the evaluation unit to determine the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

In another embodiment of the invention, the sensor systems serving to detect the electromagnetic waves within the measuring region are spatially fixed, permitting the positional and orientational determination of a spatially variable control-point reference field for instance on a patient. At least two of the sensors serving to detect the electromagnetic waves within the measuring region are preferably spatially fixed cameras, allowing an evaluation unit to videogrammetrically determine the position and orientation of the ultrasound scanning head and thus the spatial position and orientation of the tomographic ultrasound images.

In another embodiment of the invention, the sensors serving to detect the electromagnetic waves within the measuring region are cameras which are not spatially fixed, the position of the cameras being determined by the acquisition and evaluation of a spatially fixed control-point reference field, allowing the evaluation unit to videogrammetrically determine the position and orientation of the ultrasound scanning head and thus the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

In yet another implementation of the concept of this invention, the freely movable, manually guided ultrasound scanning head, the ultrasound acquisition device, the image processing unit and the positional locating device are connected to a computer-assisted surgery system (CAS).

One application of the procedure according to this invention is based on the design implementation in which the means provided on the ultrasound scanning head to emit electromagnetic waves for positional and orientational determinations are in the form of optical light sources.

Another application of the procedure according to this invention is based on the design implementation in which the means provided on the ultrasound scanning head to emit electromagnetic waves for positional and orientational determinations are in the form of infrared light emitting diodes (IRLEDs).

Another application of the procedure according to this invention is based on the design implementation in which the means provided on the ultrasound scanning head to emit electromagnetic waves for positional and orientational determinations are in the form of reflectors or electrofluorescent reflectors.

Another application of the procedure according to this invention is based on the design implementation in which the devices provided on the ultrasound scanning head to emit electromagnetic waves for positional and orientational determinations are in the form of fiber optics connected to a light source.

Yet another application of the procedure according to this invention is based on the design implementation in which the sensor systems serving to detect the electromagnetic waves within the measuring region are in the form of spatially fixed, unidimensional cameras, allowing an evaluation unit to determine the position and orientation of the ultrasound scanning head and thus the spatial position and orientation of the tomographic ultrasound images.

Another application of the procedure according to this invention is based on the design implementation in which the sensor systems serving to detect the electromagnetic waves within the measuring region are cameras which are not spatially fixed, the position of the cameras being detectable by the acquisition and evaluation of a spatially fixed control-point reference field which in turn allows the evaluation unit to determine the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

Another application of the procedure according to this invention is based on the design implementation in which the sensor systems serving to detect the electromagnetic waves within the measuring region are spatially fixed, permitting the positional and orientational determination of a spatially variable control-point reference field for instance on a patient.

Yet another application of the procedure according to this invention is based on the design implementation in which at least two sensors serving to detect the electromagnetic waves within the measuring region are spatially fixed cameras, allowing an evaluation unit to videogrammetrically determine the position and orientation of the ultrasound scanning head and thus the spatial position and orientation of the tomographic ultrasound images.

Another application of the procedure according to this invention is based on the design implementation in which the said minimum of two sensors serving to detect the electromagnetic waves within the measuring region are cameras which are not spatially fixed, the position of the cameras being determined by the acquisition and evaluation of a spatially fixed control-point reference field, allowing the evaluation unit to videogrammetrically determine the position and orientation of the ultrasound scanning head and thus the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

A different application of the procedure according to this invention is based on the design implementation in which the freely movable, manually guided ultrasound scanning head, the ultrasound acquisition device, the image processing unit and the positional locating device are connected to a computer-assisted surgery system (CAS).

Principles of optical and photogrammetric positional determination employed in this invention are described, inter alia, in the following textbook:

Jordan/Eggert/Kneissl
Handbuch der Vermessungskunde (manual of geodetic surveying)
10th edition, completely revised
Vol. IIIa/3
Photogrammetry
J. B. Metzlersche Verlagsbuchhandlung, Stuttgart, 1972 (see in particular paragraphs 144, 145, 146, 147).

As used herein, the terms 'interference measurements' and 'linear measurements' used in the patent claims refer not only to the kind of interference measurements employed for instance in laser ranging but also, and especially, to the interference effects by virtue of which optical systems can produce images (for instance central perspectives) along an image plane or line.

Moreover, the term linear measurements is intended to express longitudinal measurements along an image plane (or line) (for instance on a CCD chip), such as the linear measurement of the distance $z_1$, $z_2$ in FIG. 4 (par. 146.2, FIG. 5 in the geodetic surveying manual), as well as absolute measurements of the length of the object of interest, as employed for instance in run-length measuring methodology (for example in a GPS system).

In lieu of the method shown in FIG. 4, employing two projection planes, it is also possible to use a measuring method which is likewise based on the array principle but employs at least 3 noncolinear, unidimensional CCD chips. One such product is commercially available, by the name of Optotrak™.

If the cameras in the system according to this invention are equipped with CCD chips, it is possible for four non-coplanar points on the CCD chips of the cameras to constitute the minimum receiver base. In that case, the (linear) measurement can be made for instance by videogrammetric means or via a beam array, i.e. the images on the CCD chips are planimetrically measured. In this context, given that CCD chips permit relative measurements, the base can be selected at will which in turn allows the cameras to be positioned at will. It follows that the mutual position of the base points on the CCD chips will have to be determined which can be accomplished, without any reference volume, for instance by measuring the distance between the cameras.

One embodiment of the present invention relates to an ultrasonographic imaging system for the acquisition of ultrasound images by means of electronic data processing, characterized in that the position of the tomographic ultrasound images (a) relative to any given spatial base is unambiguously defined. The position and orientation of the tomographic ultrasound images are determined by the position and orientation of the ultrasound scanning head and a fixed control plane, which is freely selectable relative to the ultrasound scanning head and which is defined by at least three distinguishable control points that are selected in a specific relationship to the ultrasound scanning head. The spatial position and orientation of the ultrasound scanning head relative to any given base can be determined by appropriate linear measurement.

In a preferred embodiment, the linear measurements serving to determine the position and orientation of the ultrasound scanning head are made using electromagnetic waves under utilization of interference effects and/or run-length measurements. Positional and/or orientational determination of the ultrasound scanning head is preferably obtained by means of linear measurements employing electromagnetic waves.

Transmitters are preferably located at the minimum of three control points of the control plane and receivers are preferably located at a minimum of four points of the base.

Receivers are preferably located at the said minimum of three control points of the control plane and transmitters are located at a minimum of four points of the base. The control points are preferably measured at different frequencies.

Another embodiment of the invention relates to a system preferably including a freely movable, manually guided ultrasound scanning head, an ultrasound acquisition device, an image processing unit as well as a positional locating device which suitable for determining the position and orientation of the ultrasound scanning head, an evaluation unit and at least two intra-spatially operating electromagnetic-wave-detecting sensor arrays, permitting the determination of the position and orientation of the ultrasound scanning head and thus of the spatial position and orientation of the tomographic ultrasound images, characterized in that the ultrasound scanning head is provided with at least three electromagnetic wave-emitting devices.

The electromagnetic-wave-emitting devices are preferably infrared light emitting diodes (IRLEDs) or fluorescence reflectors, or reflectors. The electromagnetic-wave-emitting devices can comprise fiber optics connected to a light source.

The sensors are preferably in the form of spatially fixed unidimensional cameras enabling the evaluation unit to determine the position and orientation of the ultrasound scanning head. The sensors are preferably in the form of unidimensional cameras which are not spatially fixed and that the position of the cameras is determined by the acquisition and evaluation of the images on a spatially fixed control-point reference field, enabling the evaluation unit to determine the position and orientation of the ultrasound scanning head.

The sensors are preferably in the form of spatially fixed unidimensional cameras permitting the positional and orientational determination of a spatially variable control-point reference field located for instance on a patient.

The sensors can be in the form of cameras which are not spatially fixed, the position of the cameras being determined by the acquisition and evaluation of the images on a spatially fixed control-point reference field, enabling the evaluation unit to videogrammetrically determine the position and orientation of the ultrasound scanning head.

The sensors can be in the form of spatially fixed cameras permitting the positional and orientational determination of a spatially variable control-point reference field located for instance on a patient. The sensors can be in the form of spatially fixed cameras enabling the evaluation unit to videogrammetrically determine the position and orientation of the ultrasound scanning head.

The cameras are preferably digital cameras, such as unidimensional cameras.

The imaging system is preferably operably associated with a computer-assisted surgery system (CAS).

Another embodiment of the invention relates to a system for the acquisition of three-dimensional ultrasound images, incorporating a freely movable, manually guided ultrasound scanning head, an ultrasound acquisition device, an image processing unit as well as a positional locating device configured to determine the position and orientation of the ultrasound scanning head, an evaluation unit and at least two intra-spatially operating electromagnetic-wave-detecting sensor arrays, permitting the determination of the position and orientation of the ultrasound scanning head and thus of the spatial position and orientation of the tomographic ultrasound images, characterized in that the ultrasound scanning head is provided with at least three electromagnetic-wave-emitting devices, ensuring the spatial determination of the position and orientation of the ultrasound scanning head in relation to any given base through linear measurements.

Another embodiment of the present invention relates to a method for the acquisition of three-dimensional ultrasound images with a system incorporating a freely movable, manually guided ultrasound scanning head, an ultrasound acquisition device, an image processing unit and a positional locating device, whereby the positional locating device permits the positional and orientational determination of the ultrasound scanning head and thus of the spatial determination of the position and orientation of the tomographic images, characterized in that the positional locating device encompasses electromagnetic-wave-emitting devices mounted on the ultrasound scanning head, an evaluation unit and at least two intra-spatially operating sensor arrays detecting the said electromagnetic waves, ensuring the determination of the position and orientation of the ultrasound scanning head in relation to any given base through linear measurements.

BRIEF DESCRIPTION OF THE DRAWINGS

The present invention is described below in relation to the following drawings in which.

DETAILED DESCRIPTION OF THE PREFERRED EMBODIMENT

Figure 1:
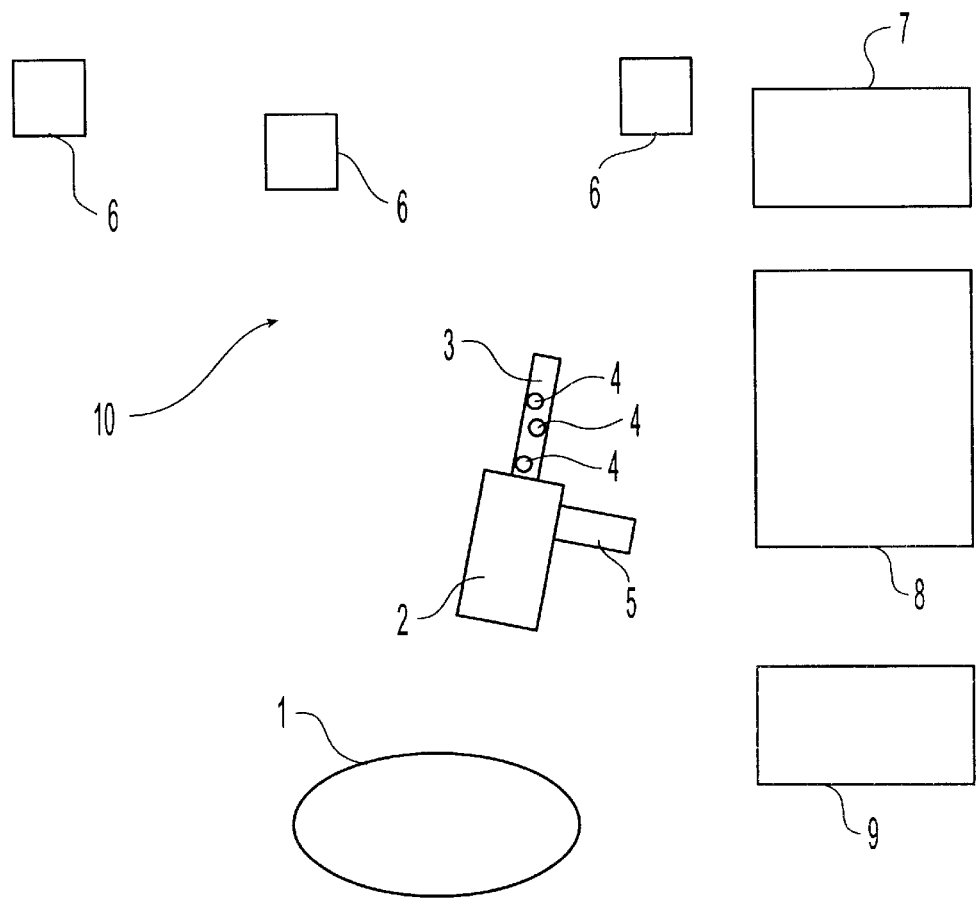
FIG. 1 is a schematic representation of one design version of the system according to this invention.

A system according to the invention as shown in FIG. 1 includes a freely movable, manually operated ultrasound scanning head 2, an ultrasound recording i.e. acquisition device 9, an image processing unit 8 and a positional locating device 10, serving to acquire three-dimensional ultrasound images of the body 1. The locating device 10 permits positional and orientational determination of the ultrasound scanning head 2 and thus the determination of the spatial position and orientation of the tomographic ultrasound images. Mounted on the ultrasound head 2 are transmitters 4 which emit electromagnetic waves. Spatially fixed cameras 6, for example digital cameras, are provided and serve to capture the said electromagnetic waves emitted by the transmitters 4. The transmitters 4 are imaged on the ultrasound scanning head 2. The evaluation unit 7 then computes from these images the position and orientation of the ultrasound scanning head 2. With the aid of a handle 5, the operator can freely move the ultrasound scanning head 2 and is thus able to assemble a complete three-dimensional tomographic image of the body 1 as derived from the three-dimensional data record defined in the image processing unit.

Figure 2:
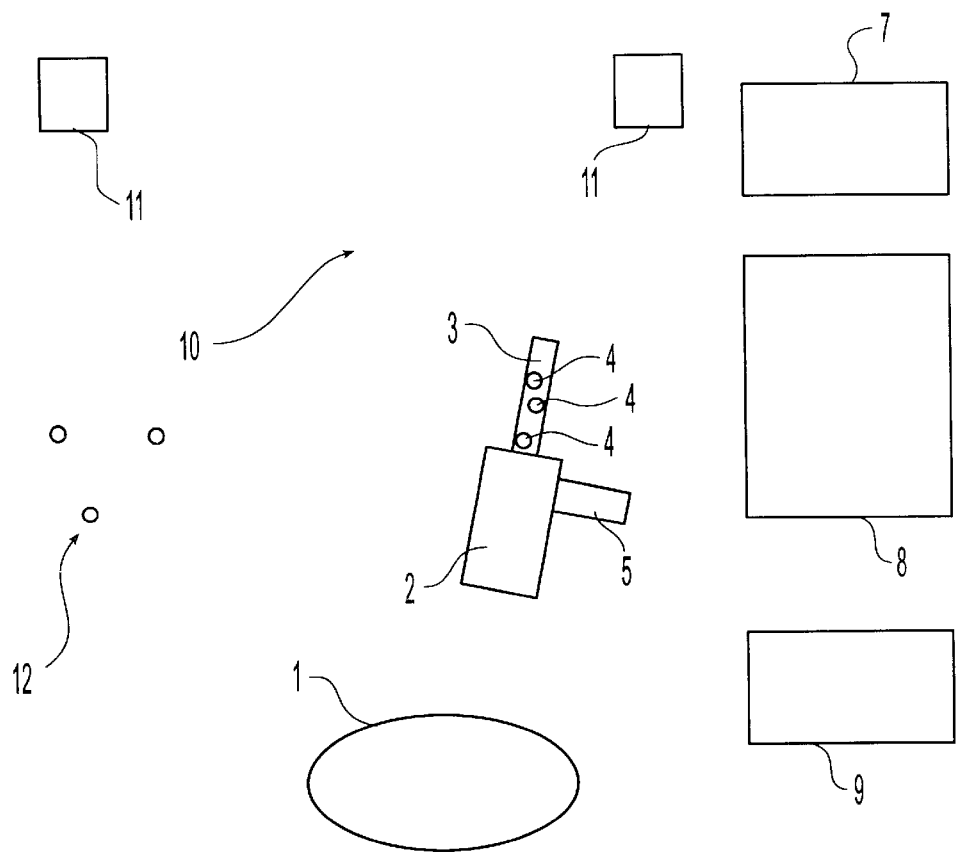
FIG. 2 is a schematic representation of another design version of the system according to this invention.

FIG. 2 shows a design version of the system according to this invention, which includes a freely movable, manually guided ultrasound scanning head 2, an ultrasound acquisition device 9, an image processing unit 8, a positional locating device 10 and a control-point reference field 12 consisting of light-emitting diodes (LED 5), serving to acquire three-dimensional ultrasonographic images of the body 1. The locating device 10 permits positional and orientational determination of the ultrasound scanning head 2 and thus the determination of the spatial position and orientation of the tomographic ultrasound images. Attached to the ultrasound scanning head 2 are transmitters 4 which emit electromagnetic waves. Cameras 6, for example digital cameras, serve to capture the said electromagnetic waves emitted by the transmitters 4. In this implementation of the invention, the cameras 6 are not spatially fixed, their position 11 being determined by the acquisition and evaluation of the images produced by a spatially fixed control-point reference field 12. As the two cameras 6 capture the electromagnetic waves emitted by the transmitters 4, these transmitters 4 are imaged on individual image planes. The evaluation unit 7 then computes from the distorted perspectives of the two images the position and orientation of the ultrasound scanning head 2. With the aid of a handle 5, the operator can freely move the ultrasound scanning head 2 and is thus able to assemble a complete three-dimensional tomographic image of the body 1 as derived from the three-dimensional data record defined in the image processing unit.

Figure 3:
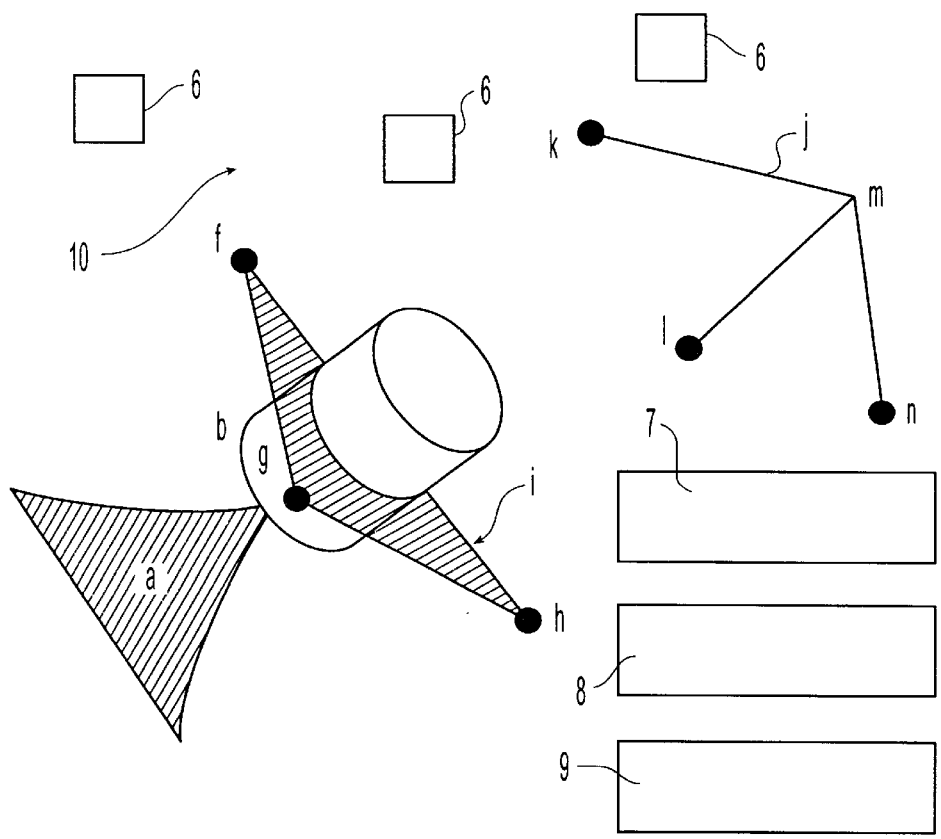
FIG. 3 is a schematic representation of yet another design version of the system according to this invention.

FIG. 3 shows a design version of the system according to this invention, which includes a freely movable, manually guided ultrasound scanning head b, an ultrasound acquisition device 9, an image processing unit 8 and a positional locating device 10 for the acquisition of ultrasound images a. The positional locating device 10 permits positional and orientational determination of the ultrasound scanning head b and thus the determination of the spatial position and orientation of the tomographic ultrasound images a. Connected to the ultrasound scanning head b are fixed transmitters f;g;h which emit electromagnetic waves. Spatially fixed cameras 6, for instance digital cameras, are provided for recording the electromagnetic waves emitted by the transmitters fg;h. The cameras 6 capture these electromagnetic waves emitted by the transmitters f;g;h and from the images thus acquired the evaluation unit 7 then calculates the position and orientation of the ultrasound scanning head b. With the aid of a handle 5, the operator can freely move the ultrasound scanning head b and is thus able to assemble a complete three-dimensional tomographic image of the body as derived from the three-dimensional data record defined in the image processing unit.

Figure 4:
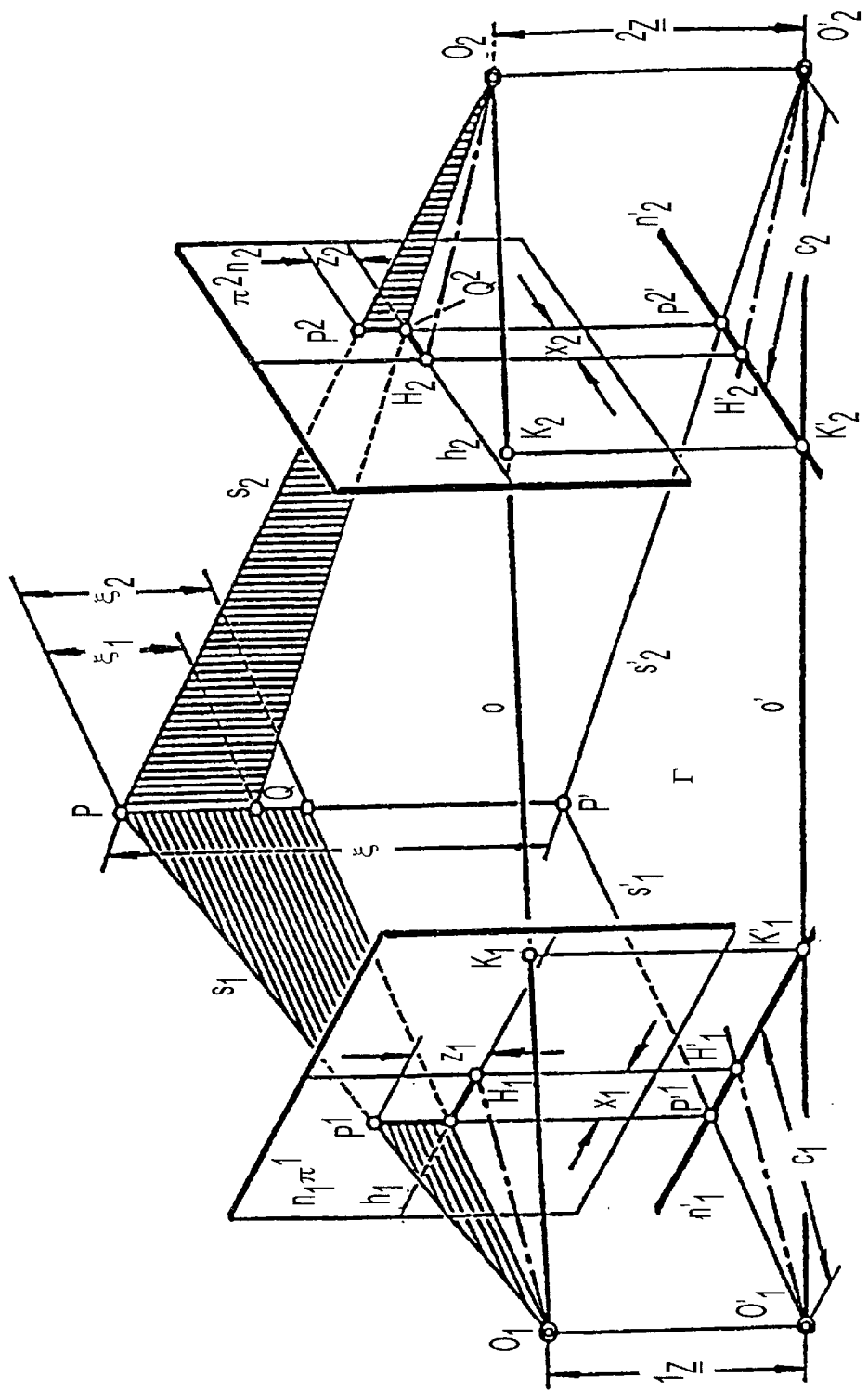
FIG. 4 is a schematic illustration serving to explain the photogrammetric procedure.

FIG. 4 is intended to explain the photogran-unetric method employed using the specific example titled "reconstruction (of the coordinates) from two perspective views with known positions of the image planes relative to each other and with known internal orientation", as per Jordan/Eggert/Kneissl, manual of geodetic surveying, 1972, page 2271:146.2 Reconstruction from two perspective views with known positions of the image planes relative to each other and with known internal orientation: Given the respective internal orientation, one knows the visual rays $[O_1]$, $[O_2]$ and their position relative to the image planes. Knowing the mutual position of the image planes thus means knowing the mutual position of the visual ray bundles. The known spatial position of $\Pi_1$, $\Pi_2$, $O_1$, $O_2$ yields the core axis o, the straight line $s=(\Pi_1 \Pi_2)$, the epipoles $K_1$, $K_2$ and the perspective allocation of the epipolar ray bundles relative to s. For any image pair $P^1$, $P^2$ tied to corresponding epipolar rays, this will ensure that the visual rays $s_1=[0_1 P^1]$ and $s_2=[0_2 P^2]$ will intersect at a spatial point P. One thus knows the position of P in the system of visual ray bundles. To determine the position of P in a given spatial reference system S one must know the position of $_{1, 2}$ within S. If the latter is not readily available, it must be determined per par. 145.3. As an example of an empirical, non-automatic reconstruction, the following will address the so-called plane-table photogrammetry.

a) In-plane-table photogrammetry (FIG. 4)<(a), in its simplest representation, with CCD chips to be assigned to the image planes $_{1, 2}$>$\Gamma$ is assumed to be a horizontal plane (planimetric plane). The image planes $\Pi_1$ $\Pi_2$ are assumed to be vertical, i.e. the main visual rays $[O_1, H_1]$, $[O_1, H_2]$ to be horizontal. $h_1$, $h_2$ constitute the image horizontal in $\Pi_1$, $\Pi_2$, x1, z1, and x2, z2 respectively, are the image coordinates in 1 and 2, respectively. The point of origin of each image coordinate system is the main point, the x-axis points extend in the horizontal direction. $ž_1$, $ž_2$ are assumed to represent the height of the central points $0_1$, $0_2$ above $\Gamma$.

It is also possible from the coordinates $x_1$, $x_2$ of any given image points $P^1$, $P^2$ to enter into the known planimetric planes $\Pi_1$, $\Pi_2$ the planimetric planes $P^1$, $P^2$', identifying the planimetric plane P' of the spatial point P to be reconstructed as a cross section of the planimetric visual-ray planes $s'_1=[O'_1 P'_1]$ and $s'_1=[O'_2 P'_2]$ (forward section). While the base line $O'_1$ $O'_2$ is applied at the map scale, the image widths and x-coordinates will be multiplied by a suitable factor in a manner which will allow $s'_1$, $s'_2$ to be traced with sufficient accuracy.

From the similar triangles $O_2PQ$ and $0_2P^2Q^2$ one can derive the height $\zeta_2$ of P above the plane $[O_2 h_2]$ via $$\zeta_2 = \frac{Z_2 O'_2 P'}{O'_2 P^1_2}$$

This yields the height $\zeta$ of P above $\Gamma$ by way of $\zeta=ž_2+\zeta_2$. By means of an analogous calculation of $\zeta=ž_1+\zeta_1$ one can compensate for any errors.

As is shown in FIG. 4, the planimetric planes $K'_1$, $K'_2$ of the epipoles $K_1$, $K_2$ are determined as intersections i.e. crossover points of the baseline $o'=[O'1O'2]$ with $\Pi'_1$, $\Pi'_2$ their respective height above $\Gamma$, meaning their position in $\Pi_1$, $\Pi_2$ is found by inverting the trapezoid $O'_1O'_2O_2O_1$, dragging along the vertical carrier line for $K_1$, and $K_2$. The epipolar rays are needed for identifying appropriate epipoles in the images of object characteristics.

If the image planes $\Pi_{1*}$, $\Pi_{2*}$ were to be in some general spatial position, one could easily revert to the case, just discussed, of vertical image planes $\Pi_1$, $\Pi_2$. One would only have to reproject $\pi^{1*}$ from $O_1$ to $\Pi_1$ and $\pi^{2*}$ from $O_2$ to $\Pi_2$. Without such reprojection, the total of the points P' per FIG. 4 would make up the normal plane of the imaged object on a plane perpendicular to $\Pi^{1*}$ and $\Pi^{2*}$ and $\zeta$ would be the distance between point P and this plane.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. An ultrasound imaging system for creating a three-dimensional ultrasound image of a patient body comprising:
   an ultrasound scanning head for acquiring a plurality of ultrasound images, the ultrasound images having a known orientation with respect to the ultrasound scanning head;
   an optical position determining device for determining a position and orientation of the ultrasound scanning head; and
   an image processor for relating the plurality of ultrasound images to one another to create the three-dimensional ultrasound image of the body.

2. The ultrasound imaging system of claim 1, wherein the optical position determining device is further configured to determine a position and orientation of the patient body.

3. The ultrasound imaging system of claim 2, wherein the system is configured to determine the position and orientation of the ultrasound images with respect to the patient body.

4. The ultrasound imaging system of claim 2, wherein the system is configured to determine the position and orientation of the three-dimensional ultrasound image with respect to the body.

5. The ultrasound imaging system of claim 1, wherein the ultrasound scanning head is freely and manually positionable.

6. The ultrasound imaging system of claim 1, wherein the ultrasound scanning head comprises electromagnetic wave emitting elements and the optical position determining device comprises electromagnetic wave receiving elements to thereby allow the position and orientation of the ultrasound scanning head to be determined.

7. The ultrasound imaging system of claim 1, wherein the electromagnetic wave emitting elements comprise light emitting diodes and the electromagnetic wave receiving elements comprise light sensitive elements.

8. An ultrasound imaging system for creating a three-dimensional ultrasound image of a patient body comprising:
   an optically trackable ultrasound scanning head for acquiring ultrasound images having a known position and orientation relative to the patient body; and
   an image processor for relating the ultrasound images to one another to create the three-dimensional ultrasound image of the body.

9. The ultrasound imaging system of claim 8, comprising an optical position determining device for determining a position and orientation of the ultrasound scanning head.

10. The ultrasound imaging system of claim 9, wherein the ultrasound scanning head comprises electromagnetic wave emitting elements and the optical position determining device comprises electromagnetic wave receiving elements to thereby allow the position and orientation of the ultrasound scanning head to be determined.

11. The ultrasound imaging system of claim 10, wherein the electromagnetic wave emitting elements comprise light emitting diodes and the electromagnetic wave receiving elements comprise light sensitive elements.

12. The ultrasound imaging system of claim 8, wherein the ultrasound scanning head is freely and manually positionable.

13. An ultrasound imaging system for creating a three-dimensional ultrasound image representative of an object comprising:
   an ultrasound scanning head for acquiring ultrasound images of the object, the ultrasound scanning head having a plurality of light emitters;
   a position determining device having light sensitive elements configured to receive light emitted by the emitters to thereby determine a position and orientation of the ultrasound scanning head,
   an image processor for relating the ultrasound images to one another to create the three-dimensional ultrasound image of the object.

14. The ultrasound imaging system of claim 13, wherein the position determining device is configured to determine a position and orientation of the object.

15. The ultrasound imaging system of claim 14, wherein the image processor is configured to determine a position and orientation of the three dimensional ultrasound image with respect to the object.

16. A method for preparing a three-dimensional ultrasound image of a patient body comprising:
   (a) moving an ultrasound head with respect to a patient body, the ultrasound head having a plurality of energy transmitters associated therewith;
   (b) acquiring a plurality of ultrasound images of the patient body by repeatedly:
      acquiring an ultrasound image of the patient body using the ultrasound head;
      receiving energy transmitted from the plurality of energy transmitters associated with the ultrasound head;
      determining, based upon energy received from the plurality of energy transmitters associated with the ultrasound head, a position and orientation of the ultrasound head; and
      determining, based on the position and orientation of the ultrasound head, at least an orientation of the ultrasound image; and
   (c) preparing a three-dimensional ultrasound image of the patient body using at least the plurality of ultrasound images acquired in the step of (b) acquiring.

17. The method of claim 16, wherein receiving energy transmitted from the plurality of energy transmitters associated with the ultrasound head comprises receiving electromagnetic waves.

18. The method of claim 16, further comprising determining a position and orientation of the three-dimensional ultrasound image with respect to the patient body.

19. The method of claim 16, wherein the step of (a) moving an ultrasound head comprises manually moving the ultrasound head with respect to the patent body.

* * * * *

UNITED STATES PATENT AND TRADEMARK OFFICE
CERTIFICATE OF CORRECTION

PATENT NO.   : 6,605,041 B2
DATED        : August 12, 2003
INVENTOR(S)  : Niklaus Emmenegger and Olaf Engfer It is certified that error appears in the above-identified patent and that said Letters Patent is hereby corrected as shown below:

<u>Column 12,</u>
Line 49, replace "patent" with -- patient -.

Signed and Sealed this

Thirtieth Day of September, 2003

JAMES E. ROGAN
*Director of the United States Patent and Trademark Office*